Figure 1:
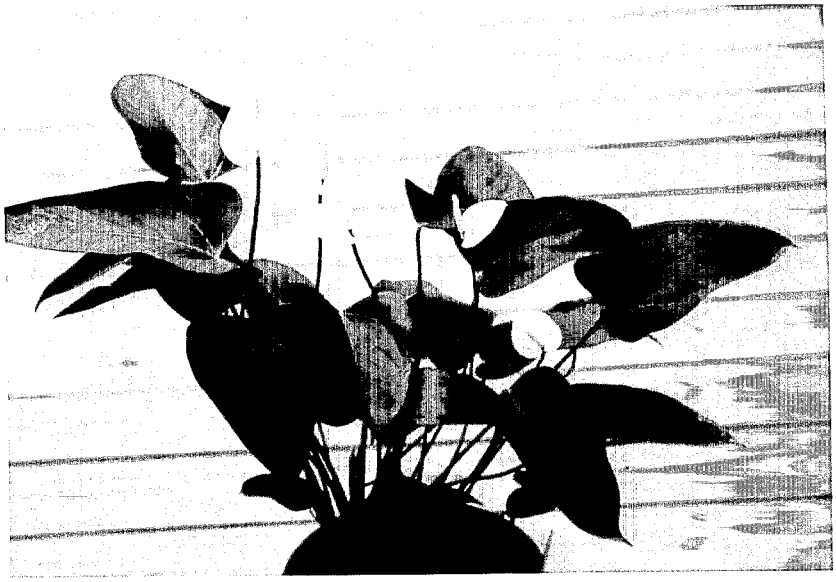

US00PP08129P

United States Patent [19]

Georgusis

[11] Patent Number: Plant 8,129

[45] Date of Patent: Feb. 2, 1993

[54] ANTHURIUM PLANT 'GEORGUSIS WHITE NUMBER 1'

[75] Inventor: James J. Georgusis, Hilo, Hi.

[73] Assignee: Oglesby Plant Laboratories, Inc., Altha, Fla.

[21] Appl. No.: 740,499

[22] Filed: Aug. 5, 1991

[51] Int. Cl.[5] ..... A01H 5/00

[52] U.S. Cl. ..... Plt./88.1

[58] Field of Search ..... Plt./88.1

*Primary Examiner*—James R. Feyrer

*Attorney, Agent, or Firm*—Frank B. Robb

[57] ABSTRACT

An Anthurium cultivar of compact freely branching form, abundant white flowers contrasting with the dark green foliage, useful as a commercial pot plant.

1 Drawing Sheet

1

This invention relates to a new and distinct Anthurium cultivar which is outstanding because of its contrasting stark white flower and dark green leaves, and primarily selected for those characteristics being so selected from a planting of Anthurium being grown near Hollywood, Fla. in a cultivated area.

Asexual reproduction of this cultivar by tissue culture was directed by me, such reproduction establishing that the plant does in fact maintain the characteristics described, in successive generations.

The cultivar may further be described as having a number of distinctive characteristics which are enumerated in the succeeding specific description but broadly stated as comprising a compact freely branching and flowering hybrid wherein the abrupt contrast between dark green foliage and numerous white flowers makes this cultivar suitable for commercial distribution as a flowering pot plant.

As will be observed from a consideration of the drawing attached hereto, the plant is in fact quite compact and yet produces both considerable foliage as well as a number of white flowers which are set off by the dark green leaves surrounding the same or adjacent thereto.

The foregoing is shown specifically in FIG. 1 which discloses the plant.

Figure 2:
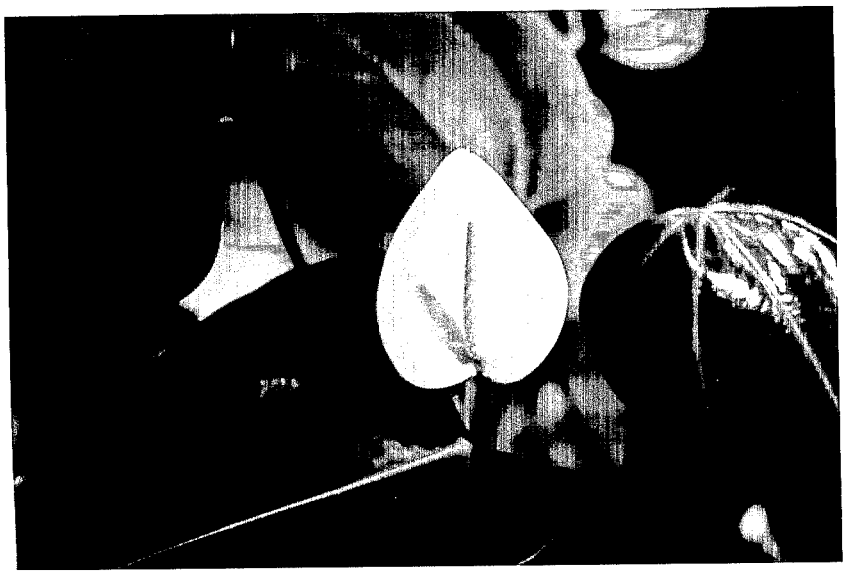

A flower alone in enlarged form with the dark green leaves in the background is shown in FIG. 2.

I have chosen to identify this new cultivar as Anthurium Georgusis White #1.

It is possible that other identification will be adopted in the trade, but the name selected will serve for the purposes hereof.

It should be noted that the plant was initially selected where grown in or near Hollywood, Fla. and has since been reproduced by plant tissue cultivar in the vicinity of Altha, Fla. with the characteristics stated, found to be maintained through successive generations as before recited.

In order to more specifically identify the cultivar descriptive details are set forth hereinafter, along with related aspects of the plant which serve to distinguish the same all colors being noted as compared with The Royal Horticultural Society Colour Chart, the measurements being made from and related to mature plants grown in the vicinity of Altha, Fla.

Parentage:

*Seed parent.*—*Anthurium* × *cultorum.*

*Pollen parent.*—*Anthurium antioquiense.*

2

*Date.*—Jun., 1982.

Propagation: Plant tissue culture, near Altha, Fla.

Plant descriptions:

*Stem.*—Smooth, green (137 C)

*Lenticels.*—Not obvious.

*Petioles.*—28–37 cm. Smooth. Color when young, green (137 C). Mature, green (137 B).

*Leaves.*—Ovate, cuspidate tip. The leaf base shape changes with overall maturity of the plant. Young plant has obtuse leaf base, changing with maturity to truncate and cordate on a fully mature plant. At maturity the leaf ranges from 19–24 cm long by 12–16 cm wide, pending age. Reflexed. Margins entire.

*Color.*—Young expanding leaf, green (137 A–138 A) adaxial (top), green (138 B) abaxial (bottom) Polished. Mature leaf, green (137 A–139 A) adaxial (top), yellow-green (146 B) abaxial (bottom). Dull appearance.

*Veins.*—Main vein (Rib) prominent near base of leaf. Both main rib and lateral veins near base of leaf protrude from leaf surface. Veins in remainder of leaf are even to somewhat sunken in the leaf surface. Rib color on a young leaf is green (137 B-C) from the base to the mid section. Rib color from the mid section to the leaf tip approximate the leaf surface color for young and mature leaves.

*Leaf sheath.*—8–10 cm long pending age. Surrounds young leaf during early development stages and is directly attached to the stem below the leaf attachment. The leaf sheath surrounding the youngest leaf is green (137 D). With age turns greyed-orange (165 B).

Flower:

*Type.*—Spathe and spadix. Spathe tightly rolled around Spadix during development. The spathe is fully opened when peduncle is fully elongated. The Spathe is polished, smooth, unpuckered, ovate, cordate base, cuspidate tip and 5–7 cm long by 4–6 cm wide. Typically, a width to length ratio 0.75:1 is consistently displayed. Flowers are consistently held above the foliage.

*Spathe Color.*—Newly open flower, light red (36 D) adaxial, white (155 D) abaxial. The light red color is more prominent under cooler growing conditions. Mature flower, white (155 C).

*Spathe veins.*—Inconspicuous. Protrude from spathe surface.

*Peduncle.*—32–36 cm long. Green (137 B) at maturity.

Reproductive organs:

*Spadix.*—4–5 cm long, 6–8 mm wide at base. Spadix color changes from the base of the spadix, red (54 D) to the middle section, red (54 C) to the tip, yellow-green (154 C) when young. With maturity, the spadix color becomes uniform red (55 D) except at the very tip red (52 D).

*Stamens.*—Anthers and filaments not clearly visible.

Flowering time: After approximately 9–12 months depending on season 1–4 blossoms will be present. Smaller flowers may occur on less mature plants.

Roots: Root developed above soil line are fleshy and non-branching. Roots developed below the soil line are fleshy and well branches with fine lateral roots.

Diseases: Initial greenhouse trials in Altha, Fla. indicate good resistance against traditional diseases.

Insects: No unusual susceptibility to insects noted to date.

The cultivar may be compared with known varieties along the following lines where observation were made on plants grown under similar conditions near Altha, Fla.

Anthurium 'Rosa': Rosa is a larger plant with a somewhat loose spreading growth habit. The leaves are a lighter green with the newest leaves a bronze color. Rosa displays larger, heart shaped, pink (48 D) flowers.

Anthurium 'Ozaki Red': Tall, leggy growth habit. Exhibits less lateral branching. Leaves generally lighter green color. Flower color Lt. red (47 A-B).

Anthurium 'Lady Jane': Similar in growth habit, leaf shape and color. Flowers wider and longer (1:2 ratio), pink (51 B). Flowers produced on young plants open even to or slightly below the foliage canopy.

Anthurium 'Southern Blush': Similar in size with a loose spreading habit. Leaves are lighter green with the new growth a bronze color. Leaf blade thinner and narrower. Leaves are held on longer petioles. The same size flower is displayed above the foliage. The flower is heart shaped, smooth, red (54 B-C), with darker margins.

I claim:

1. A new and distinct cultivar of Anthurium, substantially as described and illustrated herein, characterized particularly as to novelty by its compact form as well as its freely branching and flowering, the sharp contrast between the dark green foliage and numerous white flowers providing a cultivar well suited as a flowering pot plant having good resistance to the traditional Anthurium diseases and no unusual susceptibility to insects.

* * * * *